(12) United States Patent
Matsushita

(10) Patent No.: US 11,510,551 B2
(45) Date of Patent: Nov. 29, 2022

(54) ENDOSCOPE APPARATUS AND BALLOON

(71) Applicant: FUJIFILM Corporation, Tokyo (JP)

(72) Inventor: Motohiko Matsushita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 207 days.

(21) Appl. No.: 16/924,193

(22) Filed: Jul. 9, 2020

(65) Prior Publication Data

US 2021/0038056 A1 Feb. 11, 2021

(30) Foreign Application Priority Data

Aug. 9, 2019 (JP) .............................. JP2019-147379

(51) Int. Cl.
*A61B 1/00* (2006.01)
*A61B 1/015* (2006.01)

(52) U.S. Cl.
CPC ...... *A61B 1/00082* (2013.01); *A61B 1/00135* (2013.01); *A61B 1/015* (2013.01)

(58) Field of Classification Search
None
See application file for complete search history.

(56) References Cited

U.S. PATENT DOCUMENTS

| 4,913,701 A * | 4/1990 | Tower | ................... | A61M 25/10 29/447 |
| 6,514,450 B1 | 2/2003 | Wang et al. | | |
| 2009/0062871 A1 | 3/2009 | Chin et al. | | |
| 2009/0062872 A1 | 3/2009 | Chin et al. | | |
| 2009/0216284 A1 | 8/2009 | Chin et al. | | |
| 2009/0264822 A1 | 10/2009 | Johnson | | |

(Continued)

FOREIGN PATENT DOCUMENTS

| JP | H08118377 | 5/1996 |
| JP | 2005118375 | 5/2005 |

(Continued)

OTHER PUBLICATIONS

"Office Action of Japan Counterpart Application" with English translation thereof, dated Jun. 21, 2022, p. 1-p. 10.

*Primary Examiner* — Timothy J Neal
(74) *Attorney, Agent, or Firm* — JCIPRNET

(57) ABSTRACT

Provided are an endoscope apparatus capable of reducing a diameter of a mounting portion in a case where a balloon is mounted on an insertion part of an endoscope, and the balloon. An endoscope apparatus includes an endoscope having an insertion part, and a balloon mounted on the insertion part. The balloon includes a first sleeve part, a second sleeve part, and a balloon main body. The balloon has an inner diameter of the first sleeve part, which is 1/10 or more and 1/2 or less of an outer diameter of the insertion part, in a pre-mounting state before the balloon is mounted to the insertion part. An inner diameter of the second sleeve part may be set to 1/10 or more and 1/2 or less of the outer diameter of the insertion part. Further, the inner diameter of the second sleeve part may be larger than 1/2 of the outer diameter of the insertion part and smaller than the outer diameter of the insertion part, and an axial length of the second sleeve part of the balloon may be set to be longer than that of the first sleeve part.

13 Claims, 9 Drawing Sheets

(56) References Cited

U.S. PATENT DOCUMENTS

| | | | |
|---|---|---|---|
| 2010/0174235 A1* | 7/2010 | Yamaguchi | A61M 25/104 604/103.08 |
| 2010/0292537 A1* | 11/2010 | Ashida | G01F 1/34 600/116 |
| 2013/0190796 A1 | 7/2013 | Tilson et al. | |
| 2018/0015257 A1* | 1/2018 | Krolik | A61F 2/915 |

FOREIGN PATENT DOCUMENTS

| | | | | |
|---|---|---|---|---|
| JP | 2005185708 | 7/2005 | | |
| JP | 2008006000 | 1/2008 | | |
| JP | 200913198 A | * | 6/2009 | A61B 1/00 |
| JP | 2009131398 | 6/2009 | | |
| JP | 2009160094 | 7/2009 | | |
| JP | 2010537736 | 12/2010 | | |

\* cited by examiner

ENDOSCOPE APPARATUS AND BALLOON

CROSS-REFERENCE TO RELATED APPLICATIONS

The present application claims priority under 35 U.S.C § 119 to Japanese Patent Application No. 2019-147379 filed on Aug. 9, 2019. The above application is hereby expressly incorporated by reference, in its entirety, into the present application.

BACKGROUND OF THE INVENTION

1. Field of the Invention

The present invention relates to an endoscope apparatus and a balloon, and more particularly, to an endoscope apparatus in which a balloon is mounted to an insertion part of an endoscope, and the balloon.

2. Description of the Related Art

In an endoscope apparatus, a balloon that expands and contracts is used in various applications. For example, in an endoscope apparatus for observing a deep digestive tract such as the small intestine or the large intestine, an inflatable balloon is mounted to an insertion part of an endoscope, and the insertion part of the endoscope can be fixed inside a body by expanding the balloon.

Such a balloon is made of an elastic body such as rubber, and its end portion is formed in a cylindrical shape having a smaller diameter than an outer diameter of a mounting target (the insertion part of the endoscope) in a natural state. Further, in mounting the balloon, after covering the mounting target with the balloon while expanding the diameter of the end portion of the balloon, the end portion of the balloon is fixed to the mounting target by winding a thread from the top of the end portion of the balloon or mounting a rubber band onto the end portion of the balloon.

As another method of mounting a balloon on a mounting part, for example, the following JP2005-118375A discloses a technique of mounting, using a balloon in which both end portions are formed of a rubber material having a higher hardness than a central portion, the balloon to an insertion part of an endoscope at the end portions of the balloon having the high hardness to inflate only the central portion. JP2009-160094A discloses a technique of mounting a cylindrical portion at an end portion of a balloon to an insertion part of an endoscope, and then, reducing a pressure of a sealed chamber formed between the insertion part and the cylindrical portion to adsorb the balloon onto the endoscope, thereby mounting the balloon.

JP2008-006000A discloses an endoscope apparatus in which an end portion of a balloon unit is formed of a hard cylindrical body and a retaining ring which is a unit that prevents detachment from an insertion part of an endoscope is provided in the cylindrical body.

SUMMARY OF THE INVENTION

The balloon disclosed in JP2005-118375A has a problem that it is necessary to change a structure of a material, and thus, it is difficult to manufacture the balloon. Further, the expansion of the balloon requires an additional force for extending a body portion, and it takes time to expand the balloon.

It is difficult to reduce the size of a portion where pressure reduction is maintained in the balloon disclosed in JP2009-160094A, and in the balloon disclosed in JP2008-006000A, the diameter of the insertion part in a case where the balloon is mounted becomes large by a mounting size of the retaining ring. In a case where the diameter of the distal end of the endoscope becomes larger, it is difficult to pass through a stenosis site and an adhesion site of the intestinal tract. Further, in a case where only the endoscope is to be removed while leaving only an overtube in the body for treatment, similarly, if the diameter of the insertion part is large, it is not possible to cause the insertion part to pass through the overtube, and thus, it is not possible to remove the endoscope.

The present invention has been made in view of such circumstances, and an object of the present invention is to provide an endoscope apparatus capable of reducing a diameter of a mounting portion in a case where a balloon is mounted on an insertion part of an endoscope, and the balloon.

In order to achieve the object of the present invention, according to an aspect of the present invention, there is provided an endoscope apparatus including: an endoscope having an insertion part; and a balloon mounted to the insertion part, in which the balloon has a uniform thickness and a uniform hardness in a pre-mounting state before being mounted to the insertion part, and includes a first sleeve part that is provided at one end of the balloon and is mounted at a first position on a distal end side of the insertion part, a second sleeve part that is provided at the other end of the balloon and is mounted at a second position on a base end side of the insertion part with reference to the first position, and a balloon main body that is provided between the first sleeve part and the second sleeve part, and in which an inner diameter of the first sleeve part is 1/10 or more and 1/2 or less of an outer diameter of the insertion part, in the pre-mounting state.

In order to achieve the object of the present invention, according to another aspect of the present invention, there is provided an endoscope apparatus including: an endoscope having an insertion part; and a balloon mounted to the insertion part, in which the balloon has a uniform thickness and a uniform hardness in a pre-mounting state before being mounted to the insertion part, and includes a first sleeve part that is provided at one end of the balloon and is mounted at a first position on a distal end side of the insertion part, a second sleeve part that is provided at the other end of the balloon and is mounted at a second position on a base end side of the insertion part with reference to the first position, and a balloon main body that is provided between the first sleeve part and the second sleeve part, and in which, in a case where a Young's modulus of a material of the balloon is E, a unit of E is MPa, an inner diameter of the insertion part is D, and a unit of D is mm, and in the pre-mounting state, an inner diameter of the first sleeve part is $d_1(b)$, a unit of $d_1(b)$ is mm, an axial length of the first sleeve part is $l_1(b)$, a unit of $l_1(b)$ is mm, a thickness of the balloon is t, and a unit of t is mm, the following expression is satisfied.

$$E \times \frac{2(D - d_1(b))t}{d_1(b)(d_1(b) + 2t)} \times l_1(b) \geq 1.6E$$

In order to achieve the object of the present invention, according to still another aspect of the present invention, there is provided a balloon mounted to an insertion part of an endoscope, in which the balloon has a uniform thickness and a uniform hardness in a pre-mounting state before being mounted to the insertion part, and includes a first sleeve part that is provided at one end of the balloon and is mounted at a first position on a distal end side of the insertion part, a second sleeve part that is provided at the other end of the balloon and is mounted at a second position on a base end side of the insertion part with reference to the first position, and a balloon main body that is provided between the first sleeve part and the second sleeve part, and in which an inner diameter of the first sleeve part is 1/10 or more and 1/2 or less of an outer diameter of the insertion part, in the pre-mounting state.

In order to achieve the object of the present invention, according to still another aspect of the present invention, there is provided a balloon mounted to an insertion part of an endoscope, in which the balloon has a uniform thickness and a uniform hardness in a pre-mounting state before being mounted to the insertion part, and includes a first sleeve part that is provided at one end of the balloon and is mounted at a first position on a distal end side of the insertion part, a second sleeve part that is provided at the other end of the balloon and is mounted at a second position on a base end side of the insertion part with reference to the first position, and a balloon main body that is provided between the first sleeve part and the second sleeve part, and in which an inner diameter of the first sleeve part is 1/25 or more and 1/10 or less of a maximum inner diameter of the balloon main body, in the pre-mounting state.

In order to achieve the object of the present invention, according to still another aspect of the present invention, there is provided a balloon including: an endoscope having an insertion part; and a balloon mounted to the insertion part, wherein the balloon has a uniform thickness and a uniform hardness in a pre-mounting state before being mounted to the insertion part, and includes a first sleeve part that is provided at one end of the balloon and is mounted at a first position on a distal end side of the insertion part, a second sleeve part that is provided at the other end of the balloon and is mounted at a second position on a base end side of the insertion part with reference to the first position, and a balloon main body that is provided between the first sleeve part and the second sleeve part, and in which, in a case where a Young's modulus of a material of the balloon is E, a unit of E is MPa, an inner diameter of the insertion part is D, and a unit of D is mm, and in the pre-mounting state, an inner diameter of the first sleeve part is $d_1(b)$, a unit of $d_1(b)$ is mm, an axial length of the first sleeve part is $l_1(b)$, a unit of $l_1(b)$ is mm, a thickness of the balloon is t, and a unit of t is mm, the following expression is satisfied.

$$E \times \frac{2(D - d_1(b))t}{d_1(b)(d_1(b) + 2t)} \times l_1(b) \geq 1.6E$$

According to the present invention, it is possible to cause the first sleeve part to fixedly grip the insertion part by the contraction force of the first sleeve part expanded by inserting the insertion part. Thus, it is possible to reduce the diameter of the distal end of the insertion part of the endoscope after the balloon is mounted.

DESCRIPTION OF THE PREFERRED EMBODIMENTS

Hereinafter, an endoscope apparatus and a balloon according to the present invention will be described with reference to the accompanying drawings.

Figure 1:
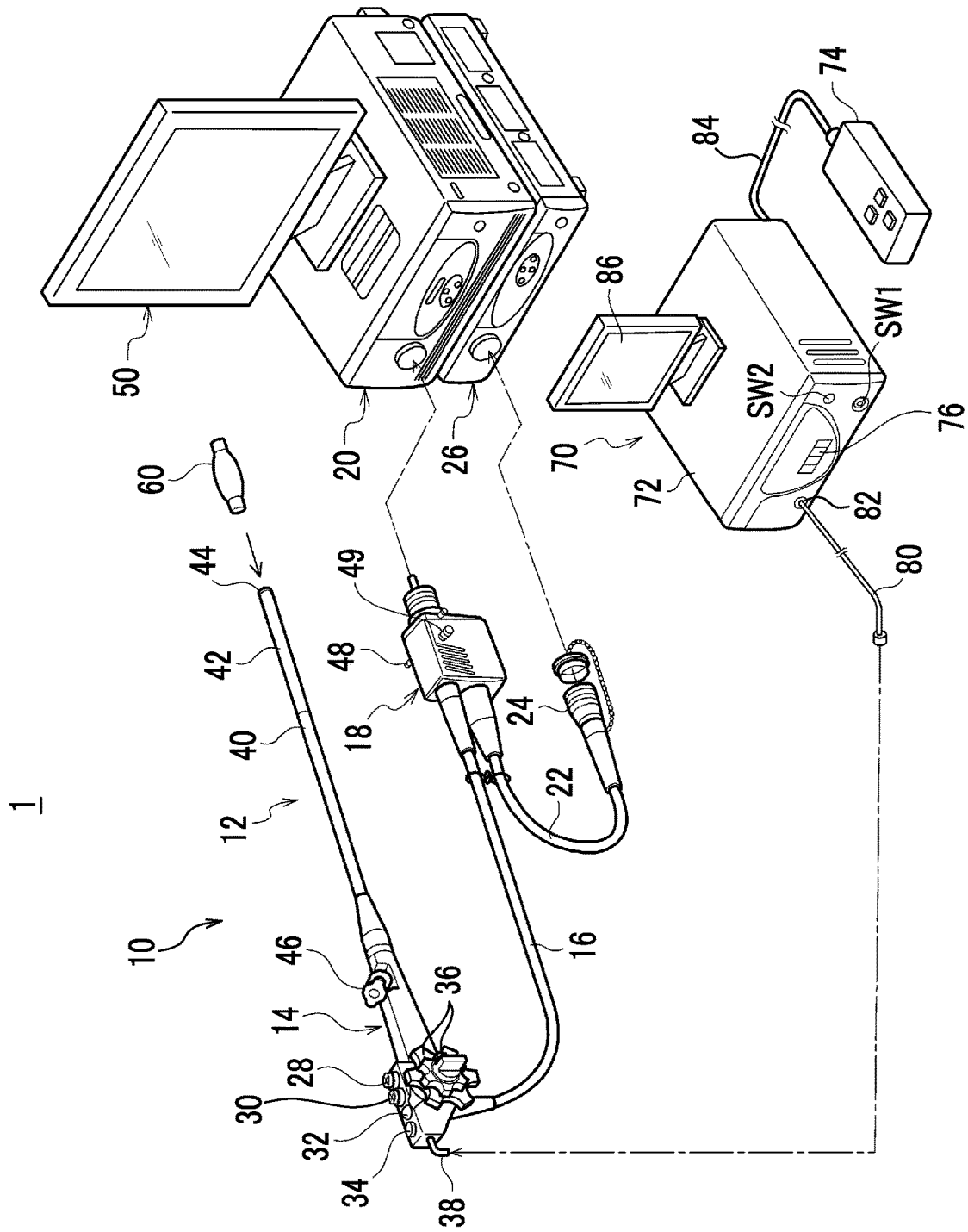
FIG. 1 is a diagram showing a system configuration of an endoscope apparatus using a balloon.

FIG. 1 is a system configuration diagram showing an example of an endoscope apparatus according to an embodiment of the present invention. As shown in FIG. 1, an endoscope apparatus 1 mainly includes an endoscope 10, and a balloon 60, as main components. Further, the endoscope apparatus 1 may include a balloon control device 70.

The endoscope 10 includes an operation part 14 and an insertion part 12 that is connected to the operation part 14 and is inserted into a body. A universal cord 16 is connected to the operation part 14, and an LG connector 18 is provided at a distal end of the universal cord 16. The LG connector 18 is detachably connected to a light source device 20, and thus, illumination light is sent to an illumination window (not shown) provided at the distal end of the insertion part 12. Further, an electric connector 24 is connected to the LG connector 18 through a cable 22, and the electric connector 24 is detachably connected to a processor 26.

An air/water supply button 28, a suction button 30, a shutter button 32, and a function switching button 34 are provided in parallel in the operation part 14, and a pair of angle knobs 36 and 36 is also provided therein.

The insertion part 12 includes a flexible part 40, a bending part 42, and a distal end part 44 in order from the side of the operation part 14. The flexible part 40 is configured by covering an outer periphery of a metal plate wound in a spiral shape with a net and coating the outer periphery, and has sufficient flexibility.

The bending part 42 is configured to be bent remotely by moving rotationally the angle knobs 36 and 36 of the operation part 14. For example, the bending part 42 has a configuration in which a plurality of cylindrical nodal rings are connected to be rotationally movable using a pin and a plurality of operation wires are inserted into the nodal rings to be guided by the pin. Further, by pushing and pulling the operation wires, the nodal rings are rotationally moved to bend the bending part 42. By bending the bending part 42, it is possible to direct the distal end part 44 in a desired direction.

Figure 2:
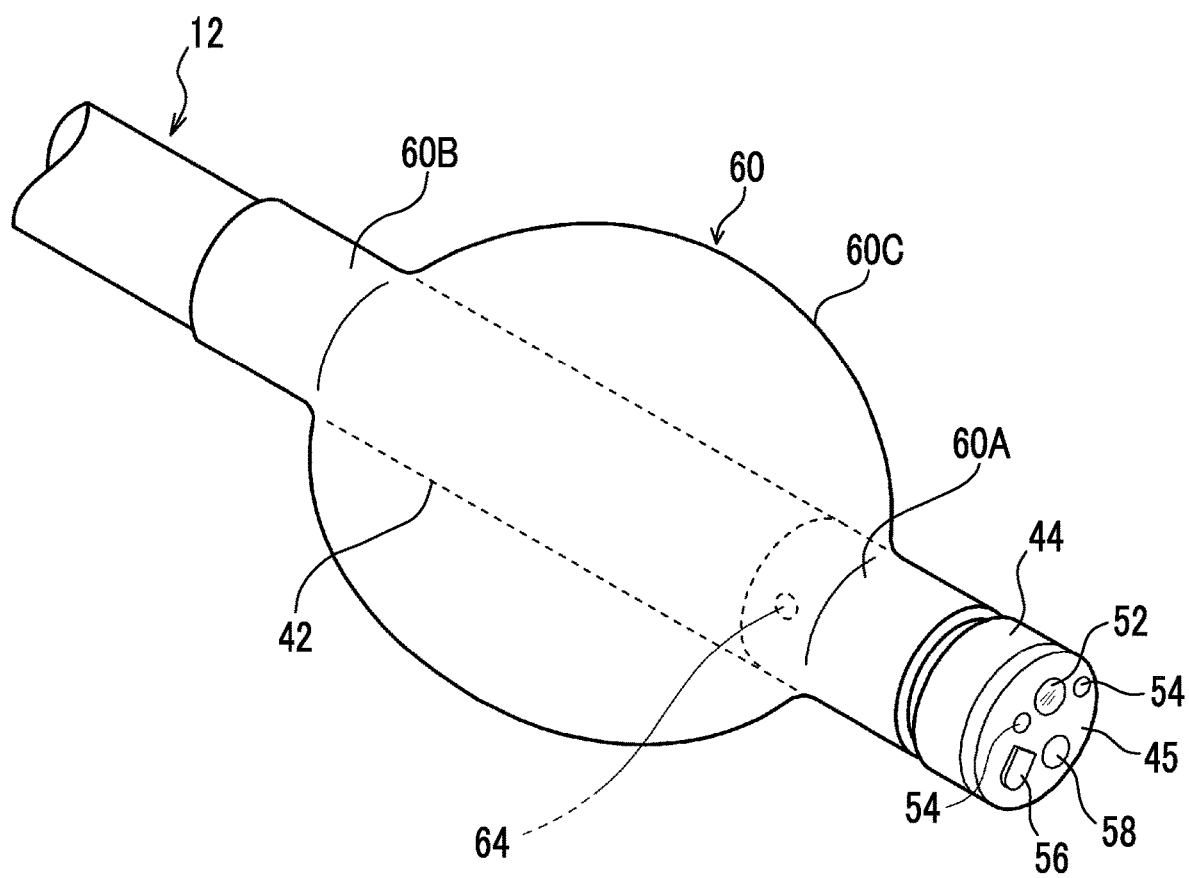
FIG. 2 is a perspective view showing a distal end part of an insertion part of an endoscope.

As shown in FIG. 2, an observation window 52, illumination windows 54 and 54, an air/water supply nozzle 56, and a forceps port 58 are provided on a distal end surface 45 of the distal end part 44. An observation optical system and an imaging element such as a complementary metal oxide semiconductor (CMOS) and a charge coupled device (CCD)

are disposed behind the observation window 52, and a signal cable is connected to a substrate that supports the imaging element. The signal cable is inserted into the insertion part 12, the operation part 14, the universal cord 16, and the like to be extended to the electric connector 24, and thus, is connected to the processor 26. Accordingly, an observation image received by the observation window 52 is formed on a light receiving surface of the imaging element, and is converted into an electric signal. The electric signal is output to the processor 26 through the signal cable, and is converted into a video signal. Thus, the observation image is displayed on a monitor 50 connected to the processor 26.

The illumination windows 54 are configured so that an illumination optical system and an emitting end of a light guide (not shown) are disposed behind the illumination window 54. The light guide is inserted into the insertion part 12, the operation part 14, and the universal cord 16, and an incident end of the light guide is disposed in the LG connector 18. Accordingly, by connecting the LG connector 18 to the light source device 20, illumination light emitted from the light source device 20 is transmitted to the illumination optical system through the light guide, and is emitted forward through the illumination window 54.

The air/water supply nozzle 56 provided at the distal end part 44 communicates with a valve (not shown) operated by the air/water supply button 28. The valve communicates with an air/water supply connector 48 provided in the LG connector 18. An air/water supply unit (not shown) is connected to the air/water supply connector 48 to supply air and water. Accordingly, by operating the air/water supply button 28, air or water is jetted from the air/water supply nozzle 56 toward the observation window 52.

The forceps port 58 provided at the distal end part 44 communicates with a forceps insertion part 46. Accordingly, by inserting a treatment tool such as a forceps through the forceps insertion part 46, it is possible to draw out the treatment tool from the forceps port 58. Further, the forceps port 58 communicates with a valve (not shown) operated by the suction button 30, and the valve is connected to the suction connector 49 of the LG connector 18. Accordingly, by connecting a suction unit (not shown) to the suction connector 49 and performing an operation using the suction button 30, it is possible to suction a lesion portion or the like through the forceps port 58.

The balloon 60 is detachably mounted on the outer periphery of the insertion part 12 of the endoscope 10. The balloon 60 is made of an elastic material such as silicone rubber. The balloon 60 includes a first sleeve part 60A that is provided at one end thereof and is mounted at a first position on a distal end side of the insertion part 12 of the endoscope 10, a second sleeve part 60B that is provided at the other end thereof and is mounted at a second position on a base end side of the insertion part 12 from the first position, and a balloon main body 60C provided between the first sleeve part 60A and the second sleeve part 60B, in which the first sleeve part 60A and the second sleeve part 60B are formed in an approximately cylindrical shape narrowed with respect to the balloon main body 60C.

The balloon 60 is disposed at a predetermined mounting position (for example, a position from the distal end part 44 to the bending part 42) by causing the insertion part 12 to pass therethrough. The first sleeve part 60A and the second sleeve part 60B are formed to have an inner diameter smaller than an outer diameter of the insertion part 12 of the endoscope 10 in a pre-mounting state. In a case where the balloon 60 is mounted on the insertion part 12, an elastic force of the first sleeve part 60A and an elastic force of the second sleeve part 60B act inward in a radial direction of the insertion part 12. That is, by being mounted to the insertion part 12, the spread first sleeve part 60A and the second sleeve part 60B contract to return to the original size. The balloon 60 is held at a predetermined position of the insertion part 12 by the contraction force of the first sleeve part 60A and the second sleeve part 60B. A specific size for mounting the balloon 60 on the insertion part 12 will be described later in detail.

A ventilation hole 64 is formed at the balloon mounting position of the insertion part 12, and the ventilation hole 64 communicates with a balloon air supply port 38 of the operation part 14 shown in FIG. 1. A tube 80 shown in FIG. 1 is connected to the balloon air supply port 38, and the balloon control device 70 is connected through the tube 80. The balloon control device 70 is a device that supplies and suctions fluid such as air into and from the balloon 60, in which the air is supplied into and suctioned from the balloon 60 according to supply and suction of the fluid (for example, air) from the balloon control device 70. The balloon 60 expands into an approximately spherical shape according to the supply of air, and sticks to the outer surface of the insertion part 12 according to the suction of air.

As shown in FIG. 1, the balloon control device 70 includes a device main body 72 and a hand switch 74 for remote control, as main components. On a front surface of the device main body 72, a power switch SW1, a stop switch SW2, and a pressure display unit 76 are provided. The pressure display unit 76 is a panel that displays a pressure value of the balloon 60, in which an error code is displayed on the pressure display unit 76 in a case where an abnormality such as balloon breakage occurs.

The tube 80 that performs the supply and suction of air into and from the balloon 60 is connected to a front surface of the device main body 72. A connection portion between the tube 80 and the device main body 72 is provided with a backflow prevention unit 82 for preventing backflow of a body fluid in a case where the balloon 60 is broken. The backflow prevention unit 82 is configured by incorporating a gas-liquid separation filter in a hollow disk-shaped case (not shown) that is detachably mounted to the device main body 72, in which inflow of liquid into the device main body 72 is prevented by the filter.

On the other hand, the hand switch 74 is provided with various switches. For example, a stop switch similar to the stop switch SW2 on the device main body 72 side, an ON/OFF switch for instructing pressurization and decompression of the balloon 60, a pause switch for retaining the pressure of the balloon 60, and the like are provided. The hand switch 74 is electrically connected to the device main body 72 through a cord 84. Although not shown in FIG. 1, the hand switch 74 is provided with a display unit that indicates an air supply state or an exhaust state of the balloon 60.

The balloon control device 70 causes air to be supplied to the balloon 60 to expand the balloon 60, and controls its air pressure at a predetermined value to retain the balloon 60 in an expanded state. Further, the balloon control device 70 causes air to be suctioned from the balloon 60 to contract the balloon 60, and controls the air pressure at a predetermined value to retain the balloon 60 in a contracted state.

The balloon control device 70 is connected to a balloon dedicated monitor 86, and displays the pressure value and the expanded and contracted state of the balloon 60 on the balloon dedicated monitor 86 in a case where the balloon 60 is expanded and contracted. The pressure value and the expanded and contracted state of the balloon 60 may be displayed on the monitor 50 to be superimposed on an observation image of the endoscope 10.

As an example of an operation method of the endoscope apparatus, the insertion part 12 is inserted in a pushing manner, and the balloon 60 is expanded as necessary to fix the insertion part 12 in the body (for example, the large intestine). In general, an air expansion pressure of the balloon 60 is set at about 5 kPa or more and 10 kPa or less. Further, after the insertion part 12 is pulled to simplify a tubular shape of the body (for example, the large intestine), the balloon 60 is contracted and the insertion part 12 is further inserted into a deep portion of the intestinal tract. For example, the insertion part 12 is inserted from the subject's anus, and in a case where the distal end of the insertion part 12 passes the sigmoid colon, the balloon 60 is expanded to fix the insertion part 12 to the intestinal tract, and the insertion part 12 is pulled to form the sigmoid colon in an approximately linear shape. Further, the balloon 60 is contracted and the distal end of the insertion part 12 is inserted into a deep portion of the intestinal tract. In this way, it is possible to insert the insertion part 12 into the deep portion of the intestinal tract. The above-described endoscope 10 may be used as a double balloon type endoscope apparatus together with an insertion auxiliary tool (not shown) with a balloon attached thereto.

Balloon

First embodiment

Figure 3:
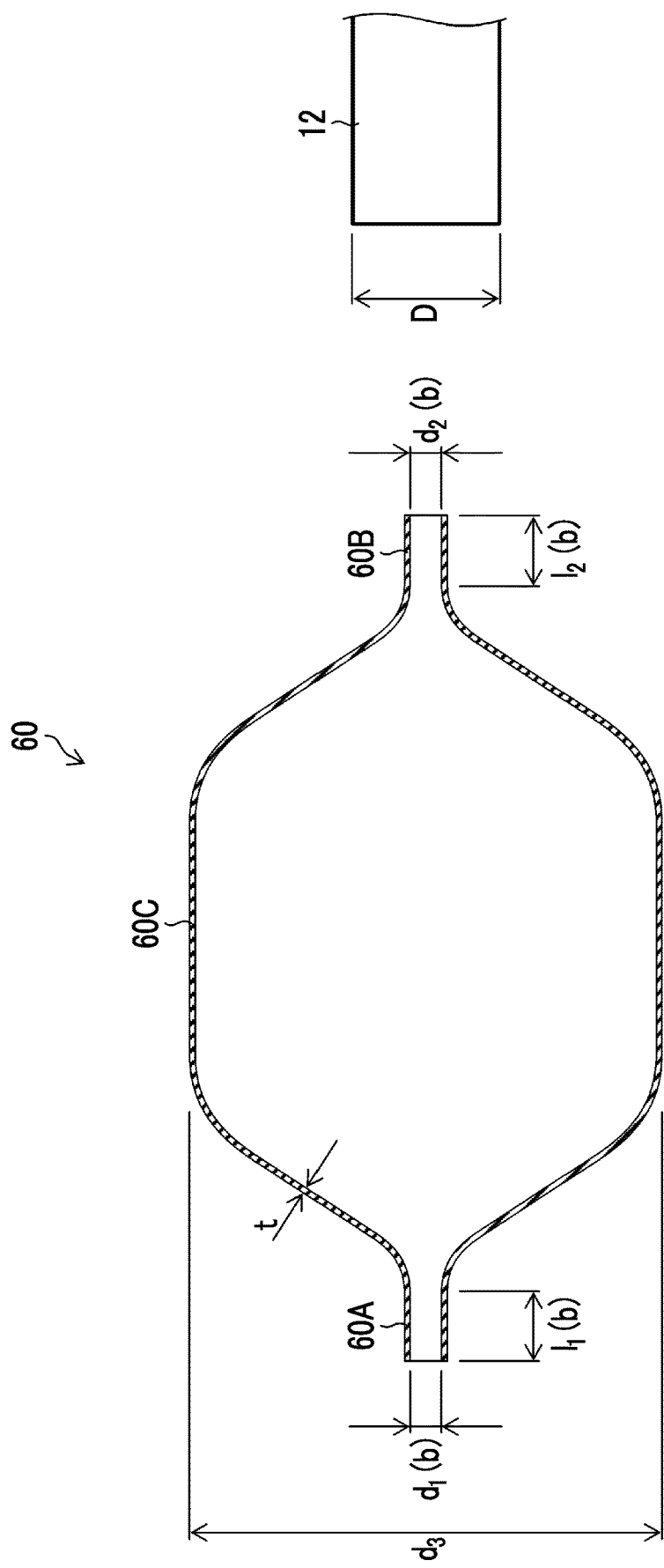
FIG. 3 is a cross-sectional view showing a configuration of a balloon according to a first embodiment.

Next, the balloon according to the present embodiment will be described. FIG. 3 is a diagram showing a configuration of the balloon 60 in a pre-mounting state. The balloon 60 has a uniform thickness and a uniform hardness in the pre-mounting state before the balloon 60 is mounted to the insertion part 12. The pre-mounting state is a natural state before the balloon 60 is mounted to the insertion part 12, and refers to a state where no force is applied from the outside. In the pre-mounting state, the first sleeve part 60A, the second sleeve part 60B, and the balloon main body 60C are in a state where there is neither expansion nor contraction. In order to make the balloon 60 have a uniform thickness and a uniform hardness, the entire balloon 60 may be formed of the same material, and the first sleeve part 60A, the second sleeve part 60B, and the balloon main body 60C may be formed of different materials, respectively.

Then, in a state before being mounted to the insertion part 12, an inner diameter $d_1(b)$ of the first sleeve part 60A is set to 1/10 or more and 1/2 or less of an outer diameter D of the insertion part 12. By setting the inner diameter $d_1(b)$ of the first sleeve part 60A within the above range with respect to the outer diameter D of the insertion part 12, it is possible to fixedly grip the first sleeve part 60A to the insertion part 12 by a contraction force of the first sleeve part 60A of the balloon 60. As described above, by mounting the balloon 60 to the insertion part 12 by the contraction force of the first sleeve part 60A, it is possible to reduce the outer diameter of the insertion part 12 after mounting the balloon 60 to the insertion part 12.

Further, in a case where a Young's modulus of the material of the balloon 60 is E [MPa], the outer diameter of the insertion part 12 is D [mm], the inner diameter of the first sleeve part 60A is $d_1(b)$ [mm], an axial length of the first sleeve part 60A is $l_1(b)$ [mm], and the thickness of the balloon 60 is t [mm], in a pre-mounting state, in the first sleeve part 60A of the balloon 60, the following expression (1) is satisfied.

$$E \times \frac{2(D - d_1(b))t}{d_1(b)(d_1(b) + 2t)} \times l_1(b) \geq 1.6E \quad (1)$$

By designing the balloon 60 so as to satisfy the above expression (1), it is possible to mount the balloon 60 to the insertion part 12 with an optimal contraction force in consideration of the material and the thickness t of the first sleeve part 60A of the balloon 60. Further, since the balloon 60 is mounted by the contraction force of the first sleeve part 60A, it is possible to reduce the outer diameter of the distal end of the insertion part 12 after the balloon 60 is mounted, so that it is possible to easily pass through a stenosis portion or the like in the body.

Since the ventilation hole 64 (see FIG. 2) for supplying air for expanding the balloon 60 is provided on the distal end side of the insertion part 12, and the first sleeve part 60A does not protrude from the distal end side of the insertion part 12, the axial length of the first sleeve part 60A is determined by the size of the insertion part 12 of the endoscope 10. Accordingly, on the side of the first sleeve part 60A, by changing the inner diameter $d_1(b)$ [mm] of the first sleeve part 60A and the thickness t [mm] of the balloon 60, it is possible to obtain a gripping force capable of gripping the balloon 60 by the first sleeve part 60A. Here, the gripping force refers to a force by which the first sleeve part 60A grips the insertion part 12 due to the contraction force of the first sleeve part 60A.

As a design that satisfies the above expression (1), the thickness t of the balloon 60 capable of obtaining the balloon gripping force in a case where the axial length $l_1(b)$ of the first sleeve part 60A is 8 mm, the outer diameter D of the insertion part 12 is 10 mm, and the Young's modulus E of the material of the balloon 60 is 0.5 MPa, and the inner diameter $d_1(b)$ of the first sleeve part 60A is changed as shown in the following Table 1 is shown.

TABLE 1

| $d_1(b)$ [mm] | 2.5 | 3 | 4 | 5 |
|---|---|---|---|---|
| T [mm] | 0.15 | 0.24 | 0.55 | 1.18 |

In a case where the inner diameter $d_1(b)$ of the first sleeve part 60A of the balloon 60 is increased, a predetermined gripping force can be obtained by increasing the thickness t of the balloon 60.

As for the inner diameter $d_1(b)$ of the first sleeve part 60A of the balloon 60, as the inner diameter $d_1(b)$ becomes smaller, the gripping force becomes greater. Further, as the inner diameter $d_1(b)$ becomes smaller, the amount of extension in being mounted to the insertion part 12 of the endoscope 10 becomes larger, and thus, it is possible to make the thickness of the balloon 60 smaller than the thickness thereof in the pre-mounting state. In order to easily mount the balloon 60 to the insertion part 12 and to reduce the diameter of the distal end of the insertion part 12 after the balloon is mounted, the inner diameter $d_1(b)$ is set to be 1/10 or more and 1/2 or less of the outer diameter D of the insertion part 12. That is, in a case where the outer diameter D of the insertion part 12 of the endoscope 10 is 10 mm, the inner diameter $d_1(b)$ is set to be 1 mm or more and 5 mm or less. More preferably, the inner diameter $d_1(b)$ is 1/5 or more and 2/5 or less of the outer diameter D of the insertion part 12, and in a case where the outer diameter D of the insertion part 12 of the endoscope 10 is 10 mm, the inner diameter $d_1(b)$ is 2 mm or more and 4 mm or less. By setting the inner diameter $d_1(b)$ of the first sleeve part 60A within the above range, it is possible to cause a jig to be easily inserted into the balloon 60 in order to mount the balloon 60 to the insertion part 12.

Further, the thickness t of the balloon 60 is preferably 0.5 mm or less, and more preferably 0.2 mm or less in the pre-mounting state, in order to reduce the thickness in a case where the balloon 60 is mounted.

Next, a method of deriving the above expression (1) and a method of fixing the balloon 60 to the insertion part 12 by the contraction force of the first sleeve part 60A by satisfying the above-mentioned expression (1) without using a fixing member will be described.

The above expression (1) is obtained on the basis of a calculation expression for shrink fit. In the present embodiment, the balloon 60 is mounted to the insertion part 12 of the endoscope by a contact pressure due to an elastic force of a material of an elastic body, that is, the material of the balloon 60, instead of heating and expanding an outer sleeve.

Figure 4:
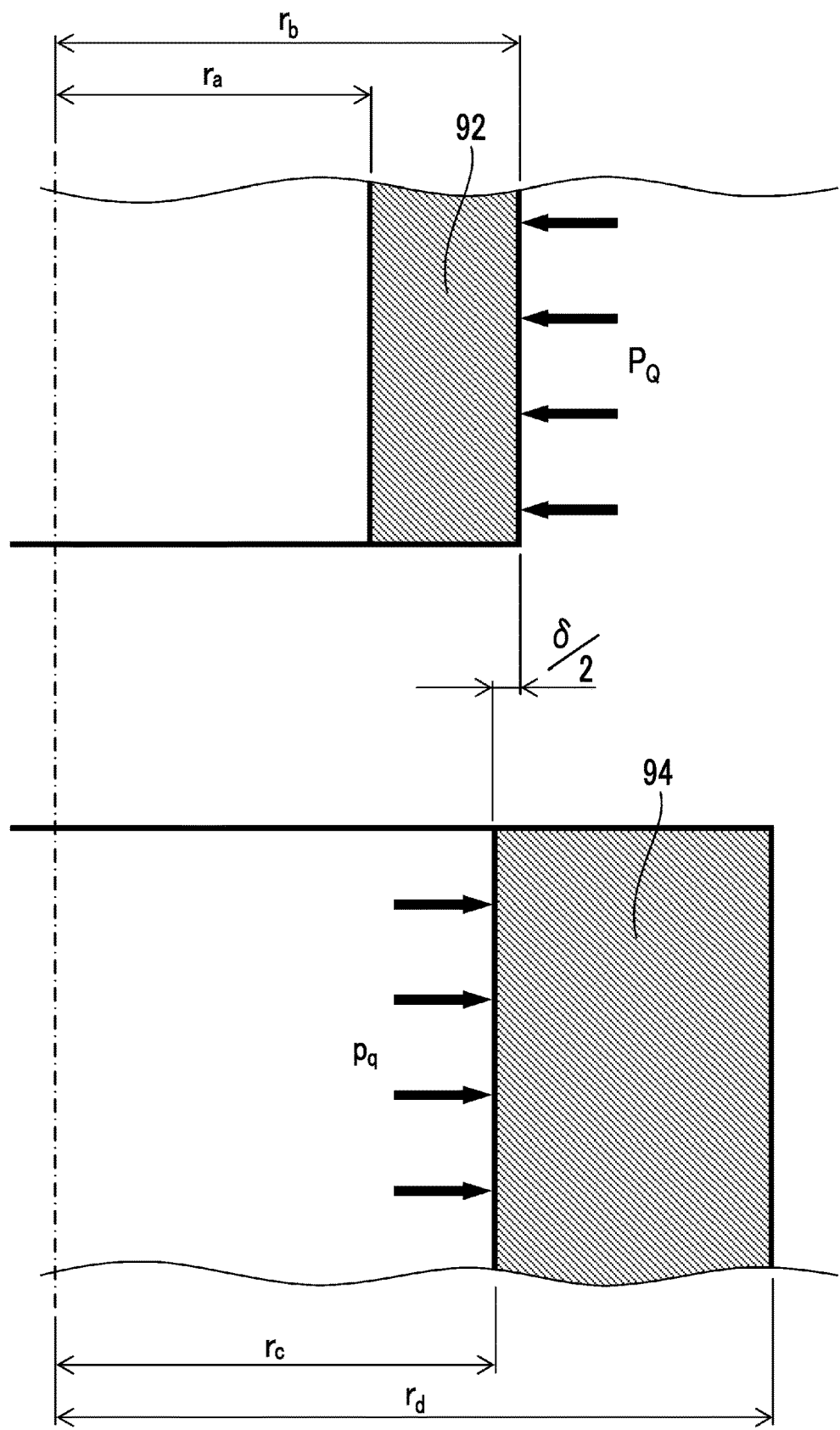
FIG. 4 is a diagram illustrating a mounting principle based on shrink fit.

FIG. 4 is a diagram illustrating dimensions of an inner sleeve 92 and an outer sleeve 94 before shrink fit, a shrink fit pressure after shrink fit, and a shrink fit allowance. As shown in FIG. 4, in a case where inner and outer radii of the inner sleeve before shrink fit are $r_a$ and $r_b$, and inner and outer radii of the outer sleeve are $r_c$ and $r_d$, it is assumed that both the outer radius $r_b$ of the inner sleeve and the inner radius $r_c$ of the outer sleeve after shrink fit become R. Here, an outer pressure $p_Q$ acts on the inner sleeve 92 and an inner pressure $p_q$ acts on the outer sleeve 94, and radial displacements $u_b$ and $u_c$ of an outer circumference of the inner sleeve and an inner circumference of the outer sleeve having the following sizes are generated. Here, $u_b$ and $u_c$ may be represented by the following expressions.

$$u_b = r_b - R \quad u_c = R - r_c$$

Further, a difference between the outer diameter of the inner sleeve and the inner diameter of the outer sleeve is called a shrink fit allowance (displacement between the inner sleeve and the outer sleeve), and as shown in FIG. 4, a shrink fit allowance δ is twice a sum of absolute values of $u_b$ and $u_c$, and is expressed by the following expression. Here, $E_1$ and $v_1$ are elastic coefficients of a material of the inner sleeve, $E_2$ and $v_2$ are elastic coefficients of a material of the outer sleeve, E is a Young's modulus, and $v$ is a Poisson's ratio.

$$\delta = 2 P_Q \left\{ \frac{r_b}{E_1} \left( \frac{r_a^2 + r_b^2}{r_b^2 - r_a^2} + v_1 \right) \right\} + \left\{ \frac{r_c}{E_2} \left( \frac{r_c^2 + r_d^2}{r_d^2 - r_c^2} + v_2 \right) \right\}$$

In a case where the above expression is applied to the present embodiment, the inner sleeve is considered as an endoscope, and the outer sleeve is considered as a balloon small diameter portion (first sleeve part 60A). Here, since the endoscope is not deformed, $E_1 = \infty$, and the first term is ignored. Thus, the following expression is derived.

$$P_Q = \frac{\delta}{2C} E_2$$

where $$\delta = 2 P_Q \left\{ \frac{r_c}{E_2} \left( \frac{r_c^2 + r_d^2}{r_d^2 - r_c^2} + v_2 \right) \right\}$$

$$C = r_c \left( \frac{r_c^2 + r_d^2}{r_d^2 - r_c^2} + v_2 \right)$$

Here, in a case where the inner diameter of the first sleeve part 60A is d (here, it is d for simplification of the expression), the inner radius $r_c$ of the outer sleeve (the first sleeve part 60A) is $r_c = d/2$, in which the thickness of the balloon 60 is further added to $r_d$, so that $r_d = t + d/2$, which is substituted. In order to simplify the notation, it is assumed that $E_2 = E$ and $v_2 = v$. The, the following expression is obtained.

$$C = \frac{d}{2} \left( \frac{\left(\frac{d}{2}\right)^2 + \left(t + \frac{d}{2}\right)^2}{\left(t + \frac{d}{2}\right)^2 - \left(\frac{d}{2}\right)^2} + v \right)$$

Here, since $t^2$ is so small that it can be ignored compared with the other terms, the following expression is obtained.

$$C = \frac{d}{2} \left( \frac{t + \frac{d}{2}}{t} + v \right)$$

Further, $v$ is negligibly small compared with $(t+D/2)/t$. Further, the radial displacement δ of the balloon 60 is $\delta = D - d$, which is obtained by subtracting the inner diameter d of the first sleeve part 60A of the balloon 60 in the pre-mounting state from the outer diameter D of the endoscope.

From the above, the following expression is obtained.

$$P_Q = \frac{E t \delta}{d \left( t + \frac{d}{2} \right)} = E \times \frac{2(D-d)t}{d(d+2t)}$$

In addition, since the above expression represents a force per unit axial length, it is possible to calculate a contact pressure in an axial length of the first sleeve part 60A by multiplying the axial length l(b) (it is assumed that d=d(b)).

$$P = E \times \frac{2(D - d(b))t}{d(b)(d(b) + 2t)} \times l(b)$$

P in the above expression represents the contact pressure of the first sleeve part 60A. By designing the first sleeve part 60A of the balloon 60 so as to satisfy the value of P≥1.6E, it is possible to mount the balloon 60 to the insertion part 12 by the contraction force of the first sleeve part 60A.

As the material used for the balloon 60, silicon rubber, latex rubber, IR rubber (polyisoprene rubber), or the like is preferably used. As the Young's modulus of the material, for example, the Young's modulus E of latex rubber is 0.5 to 1 MPa, and the Young's modulus E of silicon rubber is 5 to 50 MPa.

In the balloon 60 of the first embodiment shown in FIG. 3, the inner diameter $d_2(b)$ of the second sleeve part 60B is set to 1/10 or more and 1/2 or less of the outer diameter D of the insertion part 12. By setting the inner diameter $d_2(b)$ within the above range with respect to the outer diameter D of the insertion part 12 for the second sleeve part 60B, it is possible to cause the second sleeve part 60B to fixedly grip the insertion part 12 by the contraction force of the second sleeve part 60B.

By setting the inner diameters $d_1(b)$ and $d_2(b)$ of both the first sleeve part 60A and the second sleeve part 60B to 1/10 or more and 1/2 or less with respect to the outer diameter D of the insertion part 12, even after the balloon 60 is mounted, it is possible to reduce the diameter of the insertion part 12 on the side of the first sleeve part 60A and on the side of the second sleeve part 60B of the balloon 60. Accordingly, in a case where the insertion part 12 of the endoscope 10 is inserted into the body, it is possible to easily pass through a stenosis portion, and to pull out the endoscope 10 through the inside of an overtube.

Further, it is preferable that the maximum inner diameter $d_3$ of the balloon main body 60C is 25 mm or more and 50 mm or less according to the diameter of the intestinal tract. In addition, as the endoscope 10, an endoscope having an outer diameter D of about 10 mm at the distal end of the insertion part 12 is generally used. As described above, in a case where the balloon 60 fixedly grip the insertion part 12 by the stretching force of the first sleeve part 60A, it is preferable that the inner diameters of both the first sleeve part 60A and the second sleeve part 60B are 1/10 or more and 1/2 or less with respect to the outer diameter D of the insertion part 12, that is, 1 mm or more and 5 mm or less in a case where the outer diameter D is 10 mm.

Accordingly, considering that the inner diameter of the balloon main body 60C is 25 mm or more and 50 mm or less and the inner diameter of the first sleeve part 60A is 1 mm or more and 5 mm or less, it is preferable that the inner diameter $d_1(b)$ of the first sleeve part 60A is 1/25 or more and 1/10 or less with respect to the maximum inner diameter $d_3$ of the balloon main body 60C. By setting the inner diameter $d_1(b)$ of the first sleeve part 60A within the above range, it is possible to cause the first sleeve part 60A to fixedly grip the insertion part 12 of the endoscope.

Similarly, it is preferable that the inner diameter $d_2(b)$ of the second sleeve part 60B is 1/25 or more and 1/10 or less with respect to the maximum inner diameter $d_3$ of the balloon main body 60C. By setting the inner diameter $d_2(b)$ of the second sleeve part within the above range with respect to the maximum inner diameter $d_3$ of the balloon main body 60C, it is possible to cause the second sleeve part 60B to fixedly grip the insertion part 12 of the endoscope.

Second Embodiment

Figure 5:
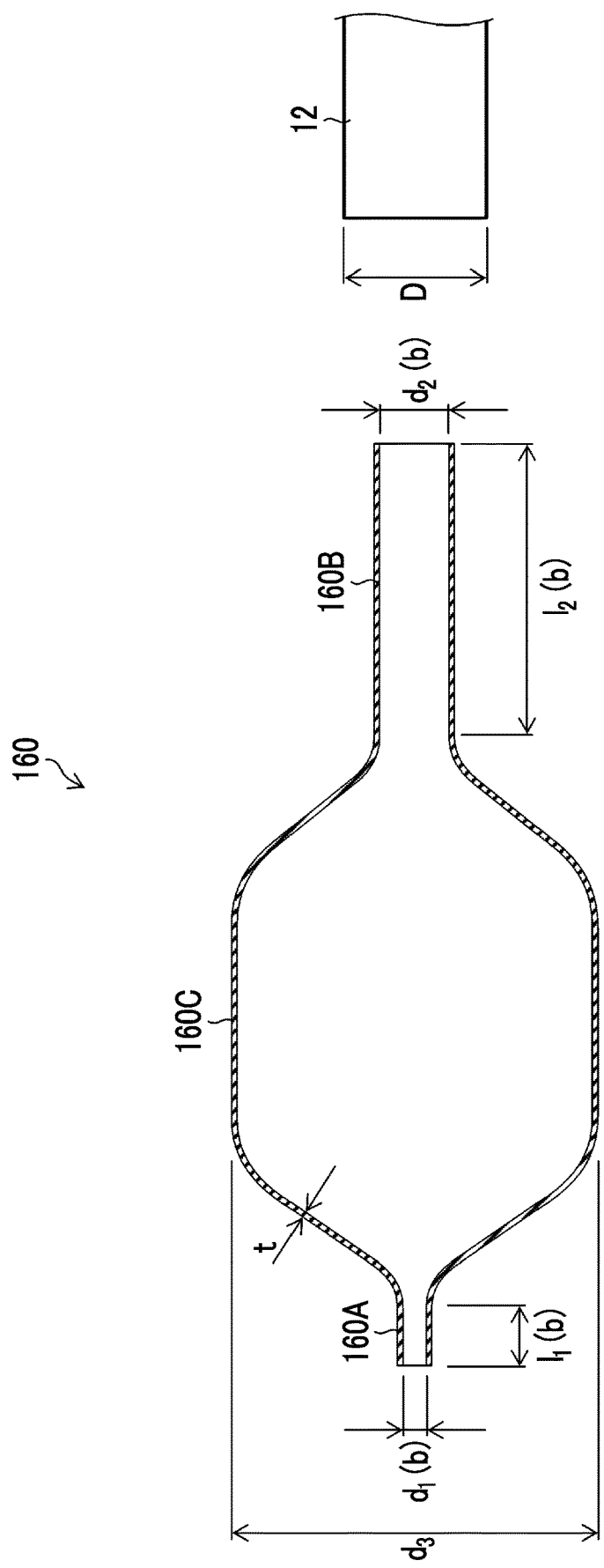
FIG. 5 is a cross-sectional view showing a configuration of a balloon according to a second embodiment.

FIG. 5 is a diagram showing a configuration of a balloon 160 in a pre-mounting state according to a second embodiment. In the balloon 160 of the second embodiment, similarly, in a pre-mounting state before the balloon 160 is mounted to the insertion part 12, the balloon 160 is configured to have a uniform thickness and a uniform hardness. Further, since a configuration of the first sleeve part 160A may be the same as the configuration of the balloon 60 of the first embodiment, description thereof will not be repeated.

In the balloon 160 according to the second embodiment, an inner diameter $d_2(b)$ of a second sleeve part 160B is larger than 1/2 of the outer diameter D of the insertion part 12 and is smaller than the outer diameter D of the insertion part 12 in a state before being mounted to the insertion part 12. Further, in an axial length of the balloon 160, an axial length $l_2(b)$ of the second sleeve part 160B is formed to be longer than an axial length $l_1(b)$ of the first sleeve part 160A.

The second sleeve part 160B of the balloon 160 according to the second embodiment is configured such that the inner diameter $d_2(b)$ in the pre-mounting state is formed to be larger than an inner diameter $d_1(b)$ of the first sleeve part 160A. Accordingly, in a case where the axial length $l_2(b)$ of the second sleeve part 160B is the same as the axial length $l_1(b)$ of the first sleeve part 160A, a contact pressure of the second sleeve part 160B in a state of being mounted to the insertion part 12 is reduced compared with that of the first sleeve part 160A. In the balloon 160 according to the second embodiment, by increasing the axial length $l_2(b)$ of the balloon 160, a contact area between the second sleeve part 160B and the insertion part 12 is becomes large, and the second sleeve part 160B fixedly grip the insertion part 12 by a predetermined contact pressure.

In the pre-mounting state, it is preferable that the inner diameter $d_2(b)$ of the second sleeve part 160B is equal to or more than 5 of the maximum inner diameter $d_3$ of the balloon main body 160C. By setting the inner diameter $d_2(b)$ of the second sleeve part 160B in the above range with respect to the maximum inner diameter $d_3$ of the balloon main body 160C, it is possible to easily pull out a mold used in manufacturing a balloon from the side of the second sleeve part 160B. As a method of manufacturing the balloon 160, for example, a method of immersing a mold in a resin solution that is a balloon material, extracting the mold from the resin solution, and drying the mold to form a balloon around the mold may be used. Then, by extracting the mold from the inside of the balloon, the balloon is manufactured. According to the balloon 160 of the second embodiment, even in a case where the inner diameter of the first sleeve part 160A is small, by setting the inner diameter of the second sleeve part 160B to be larger than that of the first sleeve part 160A, it is possible to easily pull out the mold from the side of the second sleeve part 160B.

As a method of manufacturing a balloon, in addition to the method of forming a balloon outside the mold, there is a method of forming a balloon inside a mold. As a method of forming the balloon inside the mold, first, a material of the balloon is inserted into the inside of the mold, and air is blown in so that the material of the balloon is attached to the inside of the mold. Next, the mold is cooled to solidify the balloon. Finally, the mold is opened and the balloon is extracted to mold the balloon. By forming the balloon in this manner, it is possible to form the balloon even in a case where both the first sleeve part 60A and the second sleeve part 60B have small diameters as in the balloon of the first embodiment.

In the balloon 160 of the second embodiment, similarly, since the balloon 160 is mounted to the insertion part 12 by the contraction force of the second sleeve part 160B, it is possible to reduce the diameter of the insertion part 12 even after the balloon 160 is mounted. Accordingly, it is possible to pull out only the endoscope 10 through an overtube, and as necessary in treatment, it is possible to remain only the overtube in the body.

Further, in the balloon 160 of the second embodiment, similarly, in a case where the second sleeve part 160B is configured in a pre-mounting state such that the inner diameter of the second sleeve part 160B is $d_2(b)$ [mm] and the axial length of the second sleeve part 160B is $l_2(b)$ [mm], the following expression (2) is satisfied.

$$E \times \frac{2(D - d_2(b))t}{d_2(b)(d_2(b) + 2t)} \times l_2(b) \geq 1.6E \quad (2)$$

With respect to the second sleeve part 160B, similarly, by designing the balloon 160 so as to satisfy the above expression (2), it is possible to mount the balloon 160 to the insertion part 12 by an optimal contraction force in consideration of the material and size of the second sleeve part 160B of the balloon 160. Further, since the balloon 160 is mounted by the contraction force of the second sleeve part 160B, it is possible to reduce the outer diameter after mounting even in a mounting position of the balloon 160 on the base end side of the insertion part 12. Accordingly, it is possible to pull out the endoscope 10 through an overtube while mounting the balloon 160 to the endoscope, and thus, it is possible to pull out the endoscope 10 while leaving the overtube in the body as necessary in treatment.

Since the overtube merely exists on the base end side (the operation part side) of the insertion part 12, even in a case where the axial length $l_2(b)$ of the balloon 160 on the side of the second sleeve part 160B is large, it is possible to perform treatment without affecting the operation of the endoscope. Accordingly, by changing the inner diameter $d_2(b)$ [mm] of the second sleeve part 160B and the axial length $l_2(b)$ [mm] of the second sleeve part 160B on the side of the second sleeve part 160B, it is possible to obtain a gripping force capable of gripping the balloon 160 with the second sleeve part 160B.

As a design satisfying the above expression (2), the axial length $l_2(b)$ of the second sleeve part 160B of the balloon 160 capable of obtaining a gripping force, in a case where the outer diameter D of the insertion part 12 is 10 mm, the thickness t of the balloon 160 is 0.15 mm, the Young's modulus E of the material of the balloon 160 is 0.5 MPa, and the inner diameter $d_2(b)$ of the second sleeve part 160B is changed as shown in Table 2 below, is shown.

TABLE 2

| $d_2(b)$ [mm] | 2.5 | 5 | 8 |
|---|---|---|---|
| $l_2$ [mm] | 8 | 45 | 285 |

By increasing the inner diameter $d_2(b)$ of the second sleeve part 160B of the balloon 160, the pressure in a case where the balloon is mounted is reduced, but it is possible to increase the contact area between the second sleeve part 160B and the insertion part 12, and thus, it is possible to fixedly grip the insertion part 12 by an optimal contraction force in the entire second sleeve part 160B.

It is preferable that the inner diameter $d_1(b)$ of the first sleeve part 160A with respect to the maximum inner diameter $d_3$ of the balloon main body 160C is 1/25 or more and 1/10 or less as in the first embodiment. In a case where the inner diameter $d_2(b)$ of the second sleeve part 160B is equal to or more than 1/5 of the maximum inner diameter $d_3$ of the balloon main body 160C, it is preferable that the axial length $l_2(b)$ of the second sleeve part 160B is equal to or larger than five times the axial length $l_1(b)$ of the first sleeve part 160A. By setting the inner diameter $d_2(b)$ of the second sleeve part 160B to be 1/5 or more of the maximum inner diameter $d_3$ of the balloon main body 160C, the inner diameter $d_2(b)$ of the second sleeve part 160B becomes large. Accordingly, in a case where the length $l_2(b)$ of the second sleeve part 160B is the same as the length $l_1(b)$ of the first sleeve part 160A, the contraction pressure applied to the insertion part 12 by the second sleeve part 160B becomes small. By increasing the axial length $l_2(b)$ of the second sleeve part 160B, it is possible to increase the contact area. Thus, it is possible to cause the second sleeve part 160B to fixedly grip the insertion part 12 of the endoscope.

Third Embodiment

Figure 6:
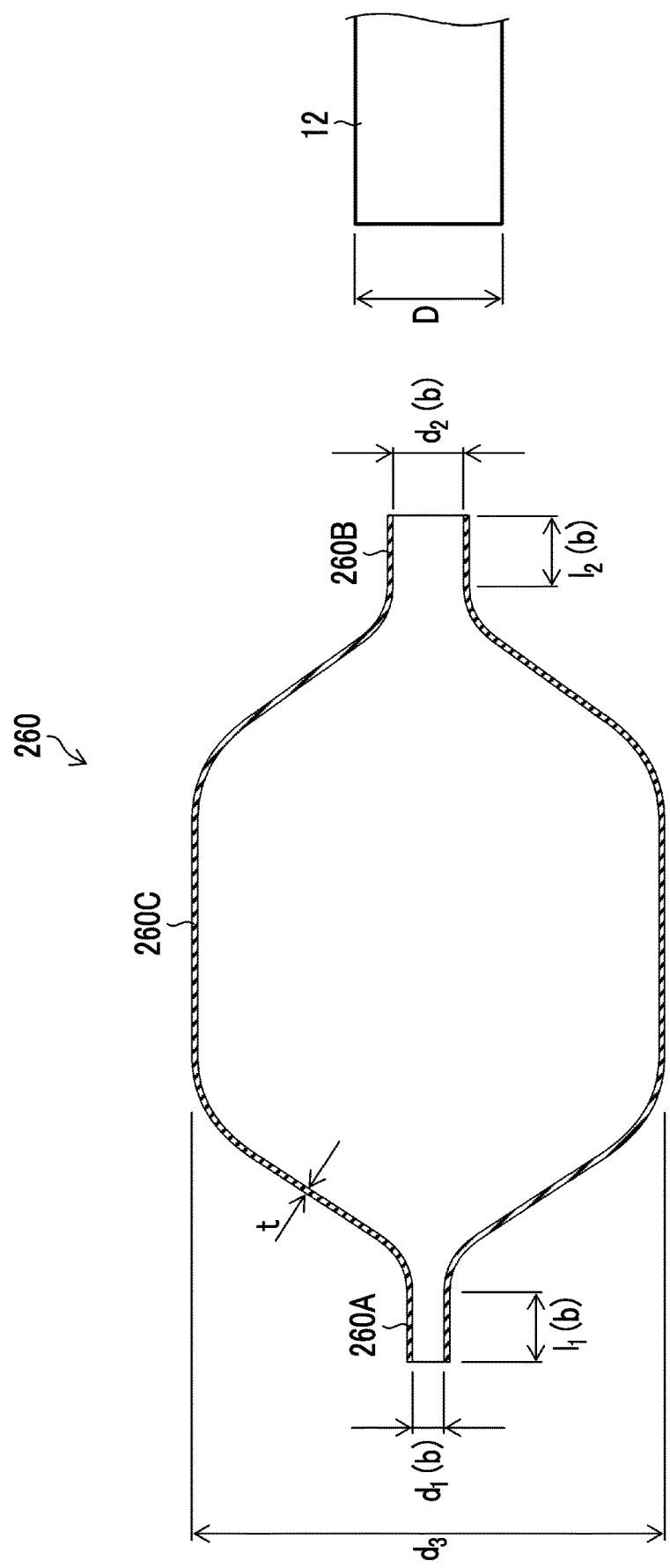
FIG. 6 is a cross-sectional view showing a configuration of a balloon according to a third embodiment.
Figure 7:
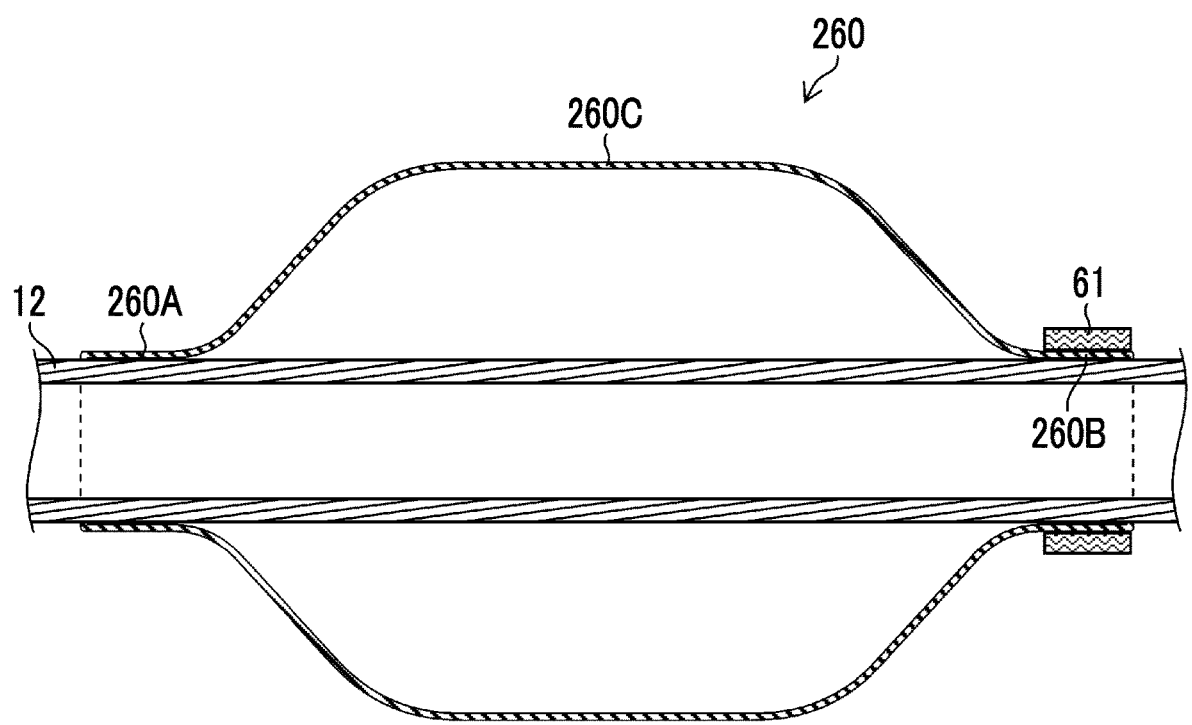
FIG. 7 is a diagram showing a mounting state of the balloon according to the third embodiment.

FIG. 6 is a diagram illustrating a configuration of a balloon in a pre-mounting state according to a third embodiment, and FIG. 7 is a diagram showing a mounting state of the balloon according to the third embodiment. With respect to a balloon 260 of the third embodiment, similarly, the balloon 260 has a uniform thickness and a uniform hardness in a pre-mounting state before the balloon 260 is mounted to the insertion part 12. Further, since the configuration of a first sleeve part 260A may be the same as the configuration of the first sleeve part 60A of the balloon 60 of the first embodiment, description thereof will not be repeated.

In the balloon 260 according to the third embodiment, an inner diameter $d_2(b)$ of a second sleeve part 260B is formed to be larger than 1/2 of the outer diameter D of the insertion part 12 in a pre-mounting state before being mounted to the insertion part 12. In such a case, in a case where an axial length of the second sleeve part 260B is not large differently from the case of the balloon 160 shown in the second embodiment, a sufficient gripping force for mounting on the insertion part 12 cannot be obtained. In a case where a sufficient contraction force cannot be obtained by only the second sleeve part 260B, as shown in FIG. 7, the second sleeve part 260B may be fixed to the insertion part 12 by the fixing member 61 that externally fitting the second sleeve part 260B to the insertion part 12.

Further, in the balloon 260 of the third embodiment, similarly, since the distal end side (the side of the first sleeve part 260A) of the insertion part 12 is reduced in diameter, in a case where the endoscope is inserted, it is possible to easily pass through a stenosis portion. In the state before the balloon 260 is mounted, by setting the inner diameter of the second sleeve part 260B to be larger than 1/2 of the outer diameter of the insertion part 12, and setting the axial length of the second sleeve part to be the same as that of the first sleeve part, it is possible to easily remove a mold in manufacturing the balloon 260.

As the fixing member 61, a rubber band having elastic force may be used. By mounting the rubber band on the outer periphery of the second sleeve part 260B mounted to the insertion part 12, it is possible to fix the insertion part 12 and the second sleeve part 260B. In addition, by winding a thread on the second sleeve part 260B using a nylon thread, it is possible to fix the insertion part 12 and the second sleeve part 260B. As another method for fixing the second sleeve part 260B to the insertion part 12, it is possible to bond the second sleeve part 260B of the balloon and the insertion part 12 with a double-sided tape for the fixing.

Method of Mounting Balloon

Figure 8:
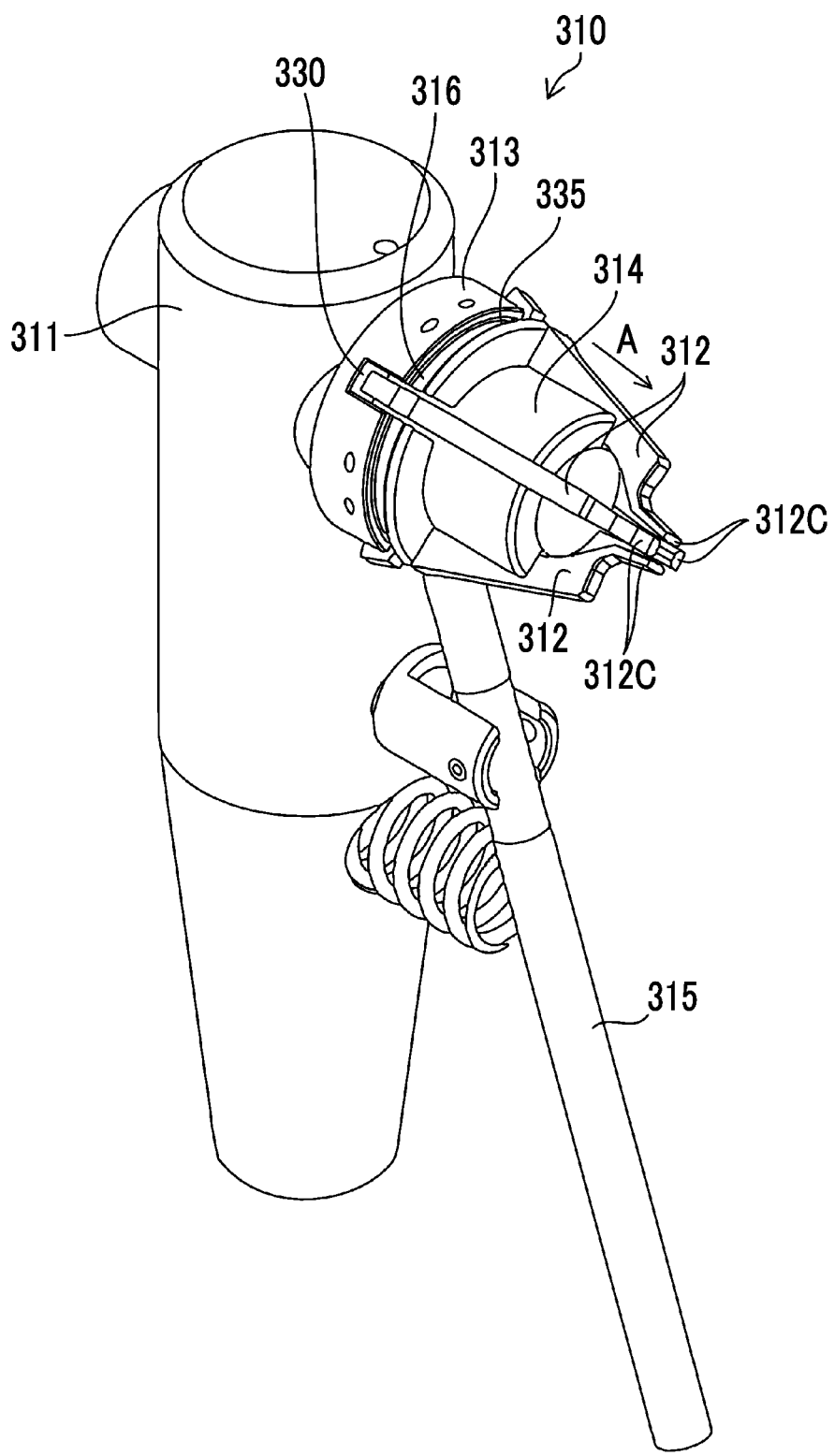
FIG. 8 is a perspective view showing an example of a balloon mounting device.

Next, a method of mounting the balloon will be described. FIG. 8 is a perspective view showing a balloon mounting device.

As shown in FIG. 8, a balloon mounting device 310 includes an arm 312, an arm holding boss (movable sleeve holding member) 313, a movable sleeve 314, a grip 311 that is a movable sleeve shift mechanism, an operation lever 315, and an arm closing ring 316. An upper part of the grip 311 has a horizontal insertion hole (not shown), and the movable sleeve 314 is movably housed in the insertion hole. The movable sleeve shift mechanism moves the movable sleeve 314 in the insertion hole in a horizontal direction with respect to the arm holding boss 313. By moving the movable sleeve 314, the shape of a receiving part 312C at a distal end of the arm 312 is changed between a reduced-diameter state and an expanded-diameter state.

The arm holding boss 313 that serves as the movable sleeve holding member is attached to the grip 311 so as to be externally fit to the movable sleeve 314. On the arm holding boss 313, four arm holding grooves 330 are formed in a diameter direction, and the arm 312 is inserted into the arm holding groove 330 to be swingably attached thereto.

An arc-shaped notch 335 is formed on an outer edge of each arm 312, and the arm closing ring 316 made of an O-ring is externally fitted in the notch 335. The arm closing ring 316 biases each arm 312 inward. In this state, the four receiving parts 312C are close to each other, so that the first sleeve part 60A and the second sleeve part 60B of the balloon 60 may be set in a natural state without being expanded by the narrowed receiving parts 312C. The setting of the balloon 60 with respect to the receiving parts 312C may be performed as follows, for example. First, the balloon 60 is wound outward from the side of the second sleeve part 60B, so that the balloon 60 is formed in which the second sleeve part 60B and the balloon main body 60C are wound. Then, the receiving parts 312C are inserted into the first sleeve part 60A of the wound balloon 60, so that the balloon 60 is set on the receiving parts 312C.

After the balloon 60 is set, the movable sleeve 314 is moved in a pushing direction of an arrow A in the insertion hole by holding the operation lever 315 to be pulled. By the movement of the movable sleeve 314, the distal end of the movable sleeve 314 presses an inner surface of each arm 312, so that each arm 312 is displaced to be opened. Due to the displacement of the arm, the first sleeve part 60A and the second sleeve part 60B of the balloon 60 set on the receiving part 312C are gradually expanded.

By moving the movable sleeve 314 in the pulling direction, the first sleeve part 60A and the second sleeve part 60B enters a state where the diameters are expanded to the maximum. In the maximum diameter-expanded state, the first sleeve part 60A and the second sleeve part 60B are expanded in size beyond the insertion part 12 of the endoscope, so that the insertion part 12 can be inserted into the movable sleeve 314.

Figure 9:
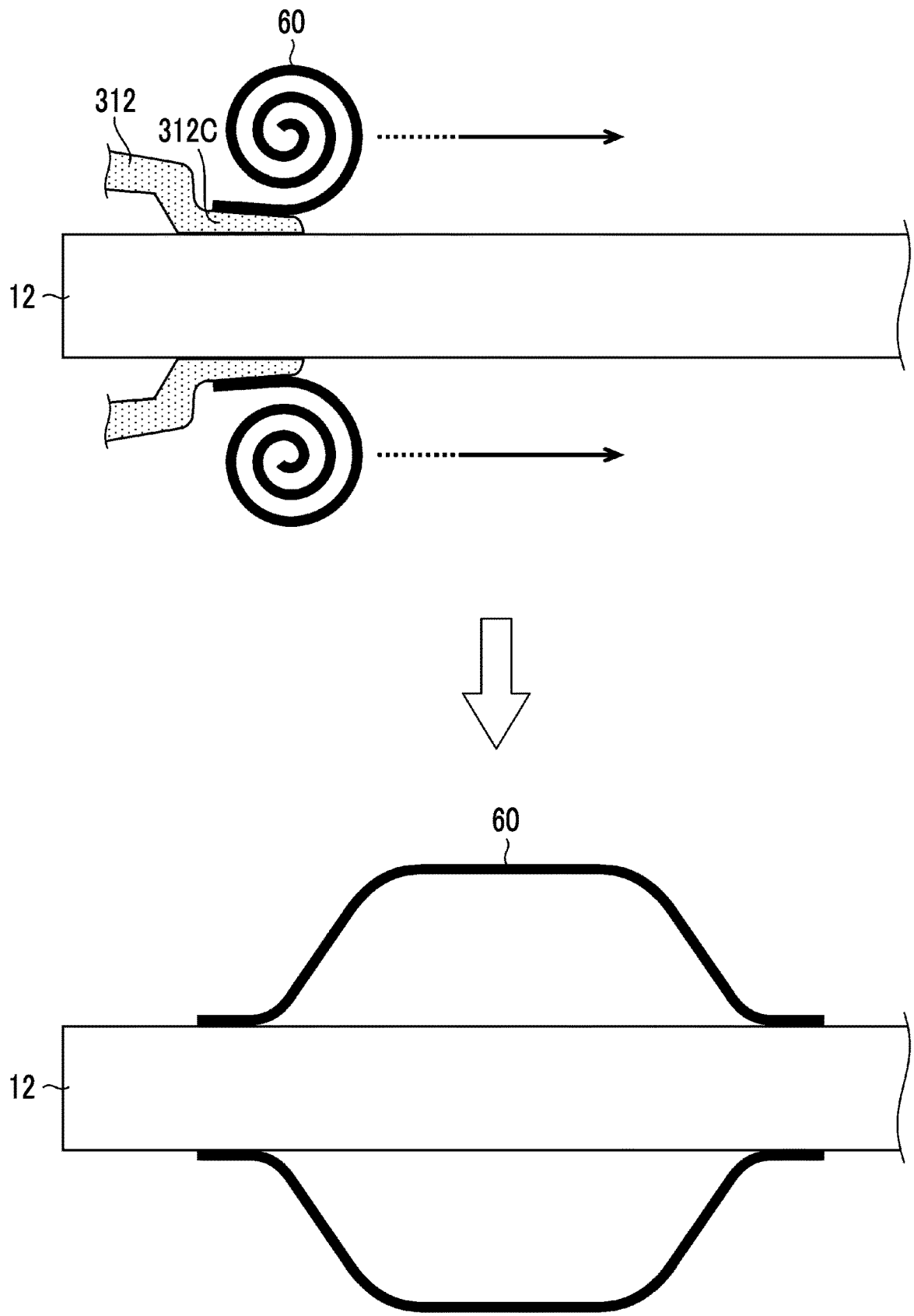
FIG. 9 is a diagram for explaining a method for attaching a balloon to an insertion part.

The insertion part 12 is put in and out, and as shown in FIG. 9, the insertion part 12 is positioned at a mounting position of the first sleeve part 60A. Further, by pulling the operation lever 315, the movable sleeve 314 moves in the pulling direction of the arrow A. In a case where the distal end surface of the movable sleeve 314 passes through the distal end of the receiving part 312C of the arm 312, the first sleeve part 60A is no longer supported by the receiving part 312C due to the passage, the diameter of the first sleeve part 60A is reduced at a set position of the insertion part 12, and the first sleeve part 60A is attached at the set position.

In the wound state, the balloon 60 set to the insertion part 12 may be attached to the insertion part 12 by rewinding the balloon 60.

As described above, according to the present embodiment, since it is possible to mount the first sleeve part 60A of the balloon 60 to the insertion part 12 of the endoscope only by a contraction force of the balloon 60, and it is not necessary to use a member for fixing the balloon 60, it is possible to reduce the diameter of the distal end of the insertion part 12. Thus, in a case where the insertion part 12 is inserted into the body, it is possible to easily pass through a stenosis portion.

Further, by mounting the second sleeve part 60B only by the contraction force of the balloon 60, it is possible to reduce the diameter of the base end side of the balloon 60. Thus, it is possible to cause the endoscope to pass through an overtube, and as necessary in treatment, it is possible to remove only the endoscope 10 with the overtube being left in the body.

EXPLANATION OF REFERENCES

1: Endoscope apparatus
10: Endoscope
12: Insertion part
14: Operation part
16: Universal cord
18: LG connector
20: Light source device
22: Cable
24: Electric connector
26: Processor
28: Air/water supply button
30: Suction button
32: Shutter button
34: Function switching button
36: Angle knob
38: Balloon air supply port
40: Flexible part
42: Bending part
44: Distal end part
45: Distal end surface
46: Forceps insertion part
48: Air/water supply connector
49: Suction connector
50: Monitor
52: Observation window
54: Illumination window
56: Air/water supply nozzle
58: Forceps port
60, 160, 260: Balloon
60A, 160A, 260A: First sleeve part
60B, 160B, 260B: Second sleeve part
60C, 160C, 260C: balloon main body
61: Fixing member
64: Ventilation hole
70: Balloon control device
72: Device main body
74: Hand switch
76: Pressure display unit
80: Tube
82: Backflow prevention unit
84: Cord
86: Balloon dedicated monitor
92: Inner sleeve
94: Outer sleeve
310: Mounting device
311: Grip
312: Arm
312C: Receiving part
313: Arm holding boss
314: Movable sleeve
315: Operation lever
316: Arm closing ring
330: Arm holding groove
335: Notch SW1: Power switch
SW2: Stop switch

What is claimed is:
1. An endoscope apparatus comprising:
an endoscope having an insertion part; and
a balloon mounted to the insertion part,
wherein the balloon has a uniform thickness and a uniform hardness in a pre-mounting state before being mounted to the insertion part, and includes
a first sleeve part that is provided at one end of the balloon and is mounted at a first position on a distal end side of the insertion part,
a second sleeve part that is provided at the other end of the balloon and is mounted at a second position on a base end side of the insertion part with reference to the first position, and
a balloon main body that is provided between the first sleeve part and the second sleeve part, and
wherein an inner diameter of the first sleeve part is 1/10 or more and 1/2 or less of an outer diameter of the insertion part, in the pre-mounting state,
wherein an inner diameter of the second sleeve part is larger than 1/2 of the outer diameter of the insertion part, in the pre-mounting state.
2. The endoscope apparatus according to claim 1,
wherein a length of the second sleeve part is longer than a length of the first sleeve part in an axial direction of the balloon.
3. The endoscope apparatus according to claim 2,
wherein the inner diameter of the second sleeve part is 1/5 or more of a maximum inner diameter of the balloon main body, in the pre-mounting state.
4. The endoscope apparatus according to claim 1,
the endoscope apparatus further comprising:
a fixing member for externally fitting and fixing the second sleeve part to the insertion part.
5. An endoscope apparatus comprising:
an endoscope having an insertion part; and
a balloon mounted to the insertion part,
wherein the balloon has a uniform thickness and a uniform hardness in a pre-mounting state before being mounted to the insertion part, and includes
a first sleeve part that is provided at one end of the balloon and is mounted at a first position on a distal end side of the insertion part,
a second sleeve part that is provided at the other end of the balloon and is mounted at a second position on a base end side of the insertion part with reference to the first position, and
a balloon main body that is provided between the first sleeve part and the second sleeve part, and
wherein, in a case where a Young's modulus of a material of the balloon is E, a unit of E is MPa, an inner diameter of the insertion part is D, and a unit of D is mm, and in the pre-mounting state, an inner diameter of the first sleeve part is $d_1(b)$, a unit of $d_1(b)$ is mm, an axial length of the first sleeve part is $l_1(b)$, a unit of $l_1(b)$ is mm, a thickness of the balloon is t, and a unit of t is mm, the following expression is satisfied:

$$E \times \frac{2(D-d_1(b))t}{d_1(b)(d_1(b)+2t)} \times l_1(b) \geq 1.6E.$$

6. The endoscope apparatus according to claim 5,
wherein in a case where in the pre-mounting state, an inner diameter of the second sleeve part is $d_2(b)$, a unit of $d_2(b)$ is mm, an axial length of the second sleeve part is $l_2(b)$, and a unit of $l_2(b)$ is mm, the following expression is satisfied:

$$E \times \frac{2(D-d_2(b))t}{d_2(b)(d_2(b)+2t)} \times l_2(b) \geq 1.6E.$$

7. A balloon mounted to an insertion part of an endoscope,
wherein the balloon has a uniform thickness and a uniform hardness in a pre-mounting state before being mounted to the insertion part, and includes
a first sleeve part that is provided at one end of the balloon and is mounted at a first position on a distal end side of the insertion part,
a second sleeve part that is provided at the other end of the balloon and is mounted at a second position on a base end side of the insertion part with reference to the first position, and
a balloon main body that is provided between the first sleeve part and the second sleeve part, and
wherein an inner diameter of the first sleeve part is 1/10 or more and 1/2 or less of an outer diameter of the insertion part, in the pre-mounting state,
wherein an inner diameter of the second sleeve part is larger than 1/2 of the outer diameter of the insertion part, in the pre-mounting state.
8. The balloon according to claim 7,
wherein a length of the second sleeve part is longer than a length of the first sleeve part in an axial direction of the balloon.
9. A balloon mounted to an insertion part of an endoscope,
wherein the balloon has a uniform thickness and a uniform hardness in a pre-mounting state before being mounted to the insertion part, and includes
a first sleeve part that is provided at one end of the balloon and is mounted at a first position on a distal end side of the insertion part,
a second sleeve part that is provided at the other end of the balloon and is mounted at a second position on a base end side of the insertion part with reference to the first position, and
a balloon main body that is provided between the first sleeve part and the second sleeve part, and
wherein an inner diameter of the first sleeve part is 1/25 or more and 1/10 or less of a maximum inner diameter of the balloon main body, in the pre-mounting state.
10. The balloon according to claim 9,
wherein an inner diameter of the second sleeve part is 1/25 or more and 1/10 or less of the maximum inner diameter of the balloon main body, in the pre-mounting state.
11. The balloon according to claim 9,
wherein an inner diameter of the second sleeve part is 1/5 or more of the maximum inner diameter of the balloon main body, in the pre-mounting state, and
wherein a length of the second sleeve part is equal to or larger than five times a length of the first sleeve part.
12. A balloon mounted to an insertion part of an endoscope,
wherein the balloon has a uniform thickness and a uniform hardness in a pre-mounting state before being mounted to the insertion part, and includes a first sleeve part that is provided at one end of the balloon and is mounted at a first position on a distal end side of the insertion part, a second sleeve part that is provided at the other end of the balloon and is mounted at a second position on a base end side of the insertion part with reference to the first position, and a balloon main body that is provided between the first sleeve part and the second sleeve part, and wherein, in a case where a Young's modulus of a material of the balloon is E, a unit of E is MPa, an inner diameter of the insertion part is D, and a unit of D is mm, and in the pre-mounting state, an inner diameter of the first sleeve part is $d_1(b)$, a unit of $d_1(b)$ is mm, an axial length of the first sleeve part is $l_1(b)$, a unit of $l_1(b)$ is mm, a thickness of the balloon is t, and a unit of t is mm, the following expression is satisfied:

$$E \times \frac{2(D - d_1(b))t}{d_1(b)(d_1(b) + 2t)} \times l_1(b) \geqq 1.6E.$$

13. The balloon according to claim 12, wherein in a case where an inner diameter of the second sleeve part is $d_2(b)$, a unit of $d_2(b)$ is mm, an axial length of the second sleeve part is $l_2(b)$, and a unit of $l_2(b)$ is mm, the following expression is satisfied:

$$E \times \frac{2(D - d_2(b))t}{d_2(b)(d_2(b) + 2t)} \times l_2(b) \geqq 1.6E.$$

* * * * *